(12) United States Patent
Puthigae et al.

(10) Patent No.: US 6,291,666 B1
(45) Date of Patent: Sep. 18, 2001

(54) SPIKE TISSUE-SPECIFIC PROMOTER

(75) Inventors: Sathish Puthigae; Ronald W. Skadsen, both of Madison, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/587,700

(22) Filed: Jun. 5, 2000

Related U.S. Application Data

(60) Provisional application No. 60/204,040, filed on May 12, 2000.

(51) Int. Cl.[7] .......................... C07H 21/02; C07H 21/04; A01H 11/00; C12N 5/00; C12N 5/04

(52) U.S. Cl. .................. 536/24.1; 536/23.1; 800/295; 435/410; 435/419

(58) Field of Search .................. 435/6, 69.1, 91.1, 435/410; 536/23.1

Primary Examiner—Robert A. Schwartzman
Assistant Examiner—M Schmidt
(74) Attorney, Agent, or Firm—Quarles & Brady, LLP

(57) ABSTRACT

A spike tissue-specific promoter has been isolated, sequenced and tested. The promoter can be used to make gene constructs including a protein-coding sequence not natively associated with the promoter and a sufficient portion of the promoter such that the portion actuates the preferential expression of the protein-coding sequence in the spike tissue of cereal grain plants.

12 Claims, 1 Drawing Sheet

SEQUENCE LISTING

```
<160> NUMBER OF SEQ ID NOS:  1

<210> SEQ ID NO 1
<211> LENGTH: 1434
<212> TYPE: DNA
<213> ORGANISM: Hordeum vulgare
<220> FEATURE:
<221> NAME/KEY: unsure
<222> LOCATION: (411)
<221> NAME/KEY: promoter
<222> LOCATION: (1187)..(1237)
<221> NAME/KEY: misc_feature
<222> LOCATION: (939)..(1014)
<223> OTHER INFORMATION: Shares partial identity with the promoter
      region of the rice anther-specific gene (RTS2) .

<400> SEQUENCE: 1
acagggcggt gcagctcggc ttggcagcgg tccgacgacc cagcggtgga tggccggcgg      60
cgggtgaggt ggcggcactg ctccttggcg gcagggcagc atgatggcgc ggggtggacg     120
gcggcgcgcc cccgacccag atctgggcca tacaagcccc atctaggttc tagcgggccg     180
gcacccgatg cgggtgcgat gtcttctgcg tggtgggtag gaggagtagc ttcgaacgag     240 gggggcggc  gacgctgacg acgtgcctgt tgcagcatgg tggcgggagc tttactgcta     300
tgatgtcccg gccggtcctg tggggccatg ggtcccgtat gctcctgcta ttgcgtccgg     360
tcggctatgt cgctgacggt ggagggtgaa cccttccccg tgccgacaat nttgttgttc     420
ctaatcccgg cttctattag tcgatgtgca ggcctctcct taccgtgtcg tgataagacg     480
gcacgggggc ttcaagacta tgttgacgca ggatgaaggt cggtctggtg gtaggctccg     540
aagagcccga ggttgggatc gggggcaact cgtgtcggtc cggccgacac cgacgcggtg     600
acaccttcgg gtgccgccga gtgttcgtgg agcgatggca atgtgtgtgg caataaagta     660
```

-continued

| | |
|---|---|
| tccctcgtcg tcgctccctc tcgaggagca tattggcatc gacgttgatg gatgagtgga | 720 |
| agtttggtgt ggtgttgcag cggtggcggc cacagtagca cacctagccg cttgggctct | 780 |
| cagtcctttg cctttagatc cgacggtcgt gactccgttt ccgagatgtt tgacagtgcg | 840 |
| atgagttccg gtccatatga ttcttcaagg ttcgcccgaa tctggtggaa aattttgctg | 900 |
| ctggtactga tgataaaagg taaatgtatt gacagtggga gtggggtttg aacccacacg | 960 |
| acctttcgta ccagaacctt aacctggcgc cttaggccaa ctcggccata tcaactcgat | 1020 |
| cgacagcaaa attttgaaca ggggaaattt tgaaaccgtc agtccggttt ctgttgctca | 1080 |
| cacgtactgc atgttgcatt gcattgcatg cctccttgct tgcacccacg tacggagaca | 1140 |
| gggctcatac atttctcccc tgcttgcacc ctccctcccg acgctcagct gcacggtata | 1200 |
| taaggataag ccaccccagc acacctctgc atctttcaac cgcacccgca cacacgacac | 1260 |
| gacacaagaa gcggagcaca cacgcaacgc acgatggcac gcaccggcgc gacggacgac | 1320 |
| gacggcagcc gccgcggcgt tactcctgct gctggcgctg gtggccaccg gcgccgccgc | 1380 |
| ggccgccggt gctggctacg agatgaacgc tgctcccgcc gccggcggtc ggat | 1434 |

SPIKE TISSUE-SPECIFIC PROMOTER

CROSS-REFERENCE TO RELATED APPLICATIONS

This application claims priority from provisional patent application Ser. No. 60/204,040 filed May 12, 2000.

STATEMENT REGARDING FEDERALLY SPONSORED RESEARCH OR DEVELOPMENT

This invention was made with United States Government support awarded by the United States Department of Agriculture, USDA No. 99-34213-7497. The United States Government has certain rights in this invention.

BACKGROUND OF THE INVENTION

The present invention relates to the general technology of plant genetic engineering and, in particular, to the identification of tissue-specific promoters and the use of these promoters to create novel genetically transformed plants.

Cereal grains, such as barley, wheat, rice, maize and oats, are the basic constituents of the food and feed industries. Because of their importance, considerable resources have been devoted toward the development of cereal grains having economically advantageous qualities. These qualities include increased vigor, disease resistance, greater yields, extended shelf-life, and enhanced nutritional content.

Unfortunately, cereal grains also serve as good hosts for a variety of fungal diseases. Several fungal diseases continue to cause heavy losses in both barley and wheat crops. One such disease is caused by the fungus *Fusarium graminearum*, which causes "scab" disease found on seed bearing spike tissues.

Aided by climatic conditions and the adoption of no-till agriculture, *Fusarium graminearum*, and its associated mycotoxins, has emerged as a major threat to food, feed and beverage products. Annually, billions of dollars worth of barley and wheat grains are lost to Fusarium, as crops infested with the fungus must be destroyed due to the lethality of grains containing more than two ppb of the Fusarium mycotoxin, "vomitoxin". At this time, there are no barley or wheat lines resistant to Fusarium and its associated fungal disease.

Ironically, barley seed already natively produces a protein, known as thionin, which inhibits Fusarium. However, in native barley, thionin is only present in sufficient quantities inside of the barley seed and not in the tissue surrounding the seed. Thus, the fungal infection can grow in the surrounding plant tissue in quantity and then infect the seed as well.

Modern techniques of recombinant DNA manipulation and genetic engineering offer the prospect of creating cereal lines which are resistant to fungal diseases. In recent years a number of genetic manipulations have been performed to modify various characteristics of cereal grains, often with commercially useful results. Such molecular approaches have definite advantages over classical breeding. The most obvious advantages are the highly directed nature of the genetic engineering process and the accelerated development of genetically engineered varieties with enhanced traits. That is, specific biochemical functionality provided by proteins produced by single genes or small related gene families, can be targeted for modification by overexpressing the particular gene involved in the target step, thereby "enhancing" or "accelerating" the targeted cellular process. Conversely, a biochemical process can be reduced or inhibited by inhibiting the expression of a gene or gene family. Approaches such as these can specifically modify a trait in an already existing, commercially useful plant without affecting other desired traits.

Gene expression is better altered by using tissue-specific promoters to target and restrict the desired genetic modifications to specific tissues in order to have a minimal effect on the overall growth and development of the plant. Promoters are DNA elements that direct the transcription of RNA in cells. Tissue-specific promoters help control the development of organisms together with other regulatory elements that determine tissue and temporal specificity of gene expression. This approach to genetic engineering, however, depends on the availability of a promoter specific enough to limit the expression of a particular transgene to the organ of interest, while simultaneously allowing expression at a high enough level to effectively modify the target gene in the desired tissues.

Presently, there are several promoters capable of expressing heterologous genes in a variety of plant tissues, but none capable of expressing solely in spike tissues. The promoters include barley B22E (Klemsdal, et al., "Primary Structure of a Novel Barley Gene Differentially Expressed in Immature Aleurone Layers," *Molecular and General Genetics*, 228:9–16 (1991)), which is expressed in aleurone cells, barley pZE40 (Smith, et al., "Temporal and Spatial Regulation of a Novel Gene in Barley Embryos," *Plant Molecular Biology*, 20:255–266 (1992), which is expressed in embryos, and a rice anther-specific gene, RTS2 (Lee and Hodges (1994), Genbank Accession: U12171; GI:607895). What is needed is a promoter that will allow the targeting of chimeric gene expression in the spike tissue of cereal grains.

BRIEF SUMMARY OF THE INVENTION

The present invention is summarized in that a promoter sequence, here designated D5, has been identified which promotes gene expression in the spike tissue of cereal grains.

The present invention includes a genetic construct comprising the promoter portion of SEQ ID NO:1 and a protein-coding sequence that is not natively associated with the promoter portion of SEQ ID NO:1. By "protein-coding sequence" we mean a sequence that encodes at least a portion of a protein and is in either the sense or antisense direction. In one embodiment the protein-coding sequence confers resistance to fungal diseases and, in particular, to diseases caused by the fungus *Fusarium graminearum.*

In another embodiment, the present invention is a genetic construct comprising a protein-coding sequence not natively associated with SEQ ID NO:1 and a sufficient portion of SEQ ID NO:1 such that the portion actuates the expression of the protein-coding sequence in the spike tissue of cereal grains. By "expression" we mean to include DNA sequences expressed into RNA and/or into protein.

In another embodiment, the present invention is a genetic construct comprising a protein-coding sequence not natively associated with SEQ ID NO:1 and a promoter sequence sufficiently homologous to SEQ ID NO:1 such that the sequence provides preferential expression in the spike tissue of cereal grains.

It is an object of the present invention to provide a promoter useful in gene expression.

It is another object of the present invention to provide a promoter capable of providing preferential expression in the spike tissue of cereal grains.

It is another object of the present invention to provide SEQ ID NO:1.

It is another object of the present invention to provide a promoter sequence isolated from a gene that is expressed only in spike tissues.

It is another object of the present invention to provide a sufficient portion of SEQ ID NO:1 such that preferential expression in spike tissue is obtained.

It is another object of the present invention to provide a transgenic plant resistant to *Fusarium graminearum*.

It is an advantage of the present invention that a transgenic plant may be created in which the transgene is expressed preferentially in spike tissue.

Other objects, features and advantages of the present invention will become apparent after examination of the specification, claims and drawings.

DETAILED DESCRIPTION OF THE INVENTION

Figure 1:
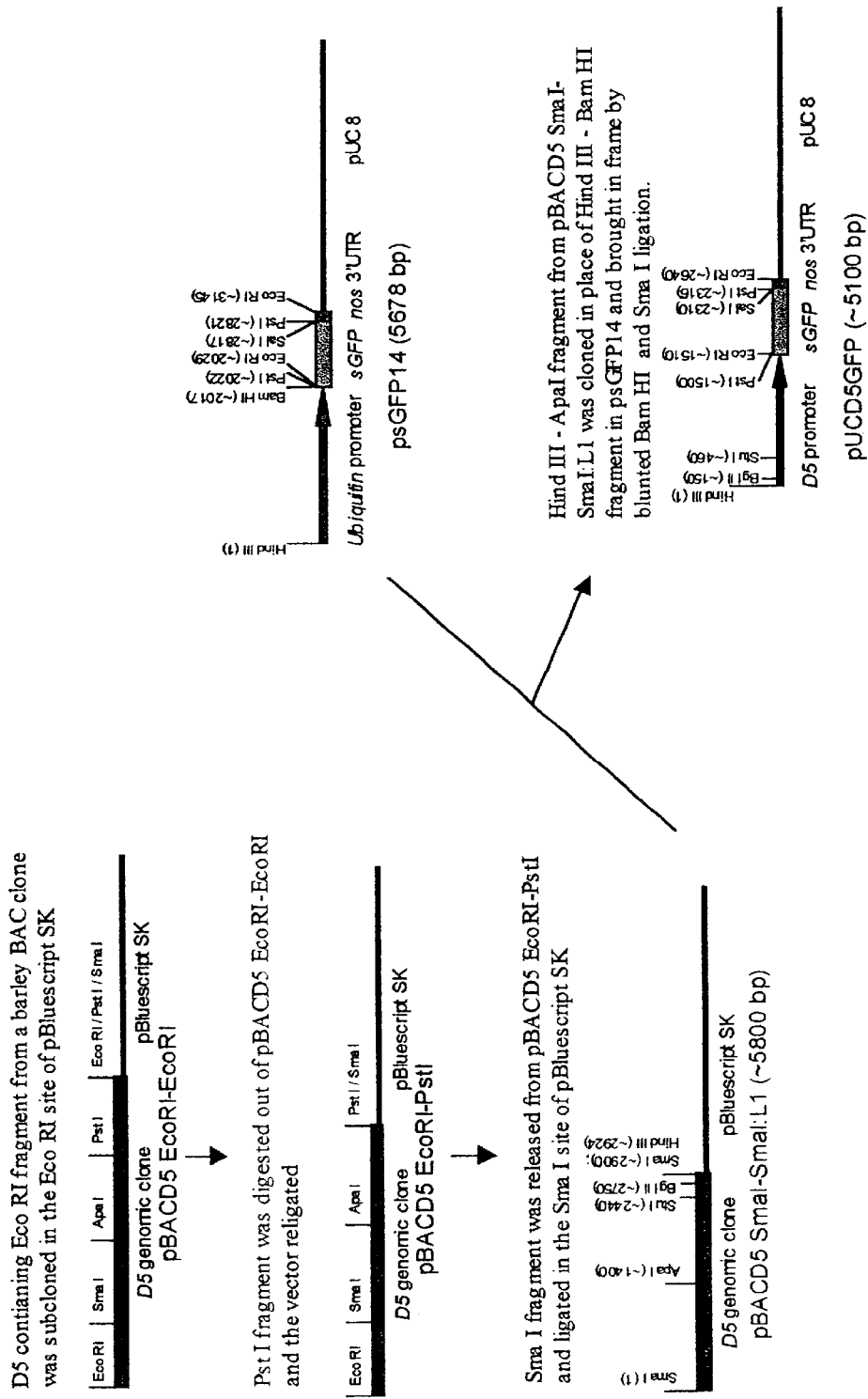
FIG. 1 illustrates the cloning of the D5 clone from a barley genomic BAC clone and the construction of a genetic construct containing the D5 promoter region.

In accordance with the present invention, a new promoter element useful in creating transgenic plants is described. This promoter sequence, identified here as the D5 promoter, is from barley (*Hordeum vulgare*, cv. Morex) and is expressed only in the spike tissue of spike-bearing plants, mainly the lemma and palea tissues that envelope the seed.

The isolation of the D5 promoter from barley is described in detail below. Basically, a barley cDNA of unknown function, here called "D5", which exhibited high expression levels in spike tissue, but not in vegetative leaves, was isolated along with its corresponding genomic clone from a barley genomic BAC library. The D5 promoter was isolated from the upstream region of the D5 genomic clone coding sequence.

The sequence of the D5 promoter region is set forth in SEQ ID NO:1. This region resides on a 1434 base pair DNA fragment and contains all sequences sufficient to confer tissue-specific expression, when connected to a protein-coding DNA sequence, and probably some additional unnecessary DNA sequence. A spike tissue-specific promoter is thus available, i.e. containing either SEQ ID NO:1 or a portion or version of SEQ ID NO:1 sufficient to effect preferential expression of a transgene in the spike tissue cells of a spike-bearing plant.

The D5 promoter region contains a sequence, located between base pairs 939 and 1014 in SEQ ID NO:1, which shares homology with an anther specific gene (RTS2) promoter region previously identified from rice. In addition, the D5 promoter region contains a sequence at base pairs 1187 to 1237 in SEQ ID NO:1, which is typical of promoter sequences in general.

One use of a spike tissue-specific promoter, such as that of the present invention, is to control the expression of target genes in transgenic plants in order to attempt to protect the seed from fungal infestation. For example, the promoter can be used to direct the expression of a gene encoding the protein thionin in the green tissues of the barley spike. This same promoter is also useful for the expression of any other desired gene in spike tissues. All or part of the base pairs of SEQ ID NO:1 may be used to direct the expression of such foreign or endogenous genes in either the sense or antisense orientation, for overexpression or suppression of native gene expression. The genes driven by the D5 promoter may be plant genes, specific anti-fungal genes, or heterologous genes, the expression of which is desired in spike tissues.

The spike tissue-specific promoter of the present invention may also be used to control the expression of target genes which affect the quality of the developing seed without affecting the growth process. Examples of such target genes include genes responsible for sugar or starch metabolism, source sink relation, organic acid balance, flavor components, pathogen resistance, soluble solids, and water/pH relations. The D5 promoter exhibits both high expression and high specificity, suggesting significant value for these and similar objectives in transgenic plants.

Creation of a D5 Promoter

The isolation of the D5 promoter using the D5 cDNA clone is described in the Examples below. The D5 cDNA clone was obtained from an mRNA molecule that was found to be expressed only in spike tissue.

The D5 clone was used to screen a barley genomic BAC library to obtain the D5 genomic clone. The D5 promoter was obtained from the D5 genomic clone. SEQ ID NO:1 discloses the sequence of the 1434 bp of the D5 promoter. Further studies are likely to show that the D5 promoter could be truncated further or have internal deletions made and still remain functional. For example, recent experiments have shown that the sequence between bases 450 to 1434 was sufficient to retain promoter activity, however, further studies are being performed to determine if the removal of bases 1 to 449 causes a quantitative loss in promoter activity. Accordingly, a promoter sequence having bases 450 to 1434 of SEQ ID NO:1 may also serve as the D5 promoter.

To obtain the D5 promoter, one could follow one of several paths. Most easily, one could create an oligonucleotide probe from the sequences disclosed in SEQ ID NO:1 and probe a barley genomic library or another plant species to obtain the entire sequence. Alternatively, one may synthetically create the sequence directly using the information from SEQ ID NO:1 below. Once the D5 cDNA sequence is obtained, one can screen a genomic library for the promoter sequence.

The Examples below disclose that SEQ ID NO:1 is sufficient to confer preferential expression of a protein-coding sequence in spike tissue. However, we envision that the promoter region of SEQ ID NO:1 could be further truncated (for example, truncations could be made from either end of the promoter sequence) and still confer the same properties because the sequence contains the transcription activators and other DNA not necessary for promoter activity. One skilled in the art of molecular biology would be able to take SEQ ID NO:1 and perform deletional analysis experiments to determine what portion of SEQ ID NO:1 is essential to confer tissue-specific expression. One could create a genetic construct with the candidate deletion mutations and a protein-coding sequence and perform experiments with transgenic plants as described below in the Examples. Occurrence of the test protein sequence preferentially in spike tissue indicates a successful deletion mutant. In this manner, and although such procedures would be tedious, one of ordinary skill in the art could determine which parts of SEQ ID NO:1 are essential for tissue-specific transcription.

In addition, it is well known that copies of genes vary from individual to individual, or variety to variety, within a species. Such variations are referred to here as allelic variations. Accordingly, there are likely to be D5-type promoters in other spike-bearing plants which may or may not have a sequence identical to SEQ ID NO:1 at each nucleotide. Such allelic variations to SEQ ID:1, as may exist, would not compromise the ability of such a variation to confer preferential expression of a protein-coding sequence in spike tissue in exactly the same manner as SEQ ID NO:1.

One skilled in the art of molecular biology would also appreciate that minor deletions, additions and mutations will not affect the function of SEQ ID NO:1. Many of the nucleotides of SEQ ID NO:1 are probably not essential for its unique function. To determine whether or not an altered sequence has sufficient homology with SEQ ID NO:1 to function identically, one would simply create the candidate mutation, deletion or alteration and create a gene construct including the altered sequence and a protein-coding sequence. This gene construct could be tested as described below in the Examples for the occurrence of the test protein predominantly in the spike tissues of a transgenic plant.

Assay of Candidate Promoter

Once a candidate genomic sequence has been isolated, one may wish to determine whether or not this DNA sequence is a D5 promoter. One could determine the DNA sequence of a putative promoter using techniques familiar to one of ordinary skill in the art of plant molecular biology. If the candidate sequence is identical or homologous to a portion of SEQ ID NO:1, then the sequence is a suitable D5 promoter. Another category of suitable D5 promoters would have at least about 75% DNA sequence identity with SEQ ID NO:1, and would also exhibit spike tissue-specific promoter activity.

If the putative spike tissue-specific promoter is not identical, however, and is closely homologous, i.e. at least about 75% homologous, one may have isolated a copy of an allelic D5 promoter. One would wish to do a functional assay to determine whether or not this sequence was sufficiently homologous to SEQ ID NO:1 and suitable for the present invention. Thus as used here the term D5 promoter is intended to encompass not only the sequence set forth in SEQ ID NO:1 below and truncations and deletions thereof but also allelic variants and homologs thereof from other plants species which have at least 75% DNA sequence identity with SEQ ID NO:1 below and which are capable of demonstrating spike tissue-specific promoter activity by the test methodology described here.

To make this determination, one could follow the examples described below and attach the candidate promoter to a reporter protein coding sequence, such as the GUS sequence encoding the enzyme beta-glucuronidase. The sequence of the GUS gene is described in U.S. Pat. No. 5,268,463. Transformation of a plant with an expression cassette including the GUS sequence allows one to determine whether or not the GUS reporter sequence is expressed in only the spike tissues, is constitutively expressed, or is not expressed at all. Only a result indicating that the reporter sequence is only expressed in spike tissues and not other tissues would indicate a suitable promoter. Thus a suitable method is envisioned to test candidate D5 promoters to demonstrate the tissue specificity of those promoters.

Alternatively, the candidate sequence could replace the Ubi1 promoter in the psGFP14 vector and be transformed into barley plants as described below.

Genetic Construct

The present invention enables the promoter sequence to be combined with a protein-coding sequence in a genetic construct. Commonly used methods of molecular biology well-known to those of skill in the art may be used to manipulate the DNA sequence.

By "genetic construct" we mean any of a variety of ways of combining the promoter sequence with the protein-coding sequence or an antisense sequence in a manner that operably connects the promoter sequence with the protein-coding sequence. Typically, the promoter sequence will be 5' or "upstream" of the protein-coding nucleotide sequence or antisense sequence. The promoter will be able to promote transcriptional activity using the protein-coding sequence or antisense sequence as the template.

For example, the promoter sequence and the protein-coding sequence may be combined together on a plasmid or bacterial vector or they can be assembled in vitro. Other functional sequences, such as secretion signals, polyadenylation and termination sequences, may be added to the gene construct. Alternatively, the protein-coding and promoter sequences may be combined together with other needed functional sequences and used without a vector.

By "protein-coding sequence" we mean any nucleotide sequence capable of transcription into mRNA and translation into protein. On occasion, it may be desired to turn a protein-coding sequence into an antisense orientation to create an antisense version of the construct to inhibit native gene expression levels. As used here, the term protein coding sequence is intended to be applicable to such a sequence in either sense or antisense orientation.

In one embodiment of the invention, the protein-coding sequence includes, without limitation, genes capable of conferring resistance to fungal diseases. In particular, the protein-coding sequence includes those genes capable of conferring resistance to *Fusarium graminearum*. One such gene includes, without limitation, a native thionin gene (Rodriguez-Palenzuela et al., "Nucleotide Sequence and Endosperm-Specific Expression of the Structural Gene for the Toxin Alpha-Hordothionin in Barley (*Hordeum vulgare* L.)" *Gene,* 70:271–281 (1988)), the expression of which in the extracellular space of the lemma/palea and pericarp of the spike may confer resistance to Fusarium infestation.

The genetic construct may be created using either plasmid or viral vectors or other methods known in the art of molecular biology to create a construct suitable for transformation into a plant cell. We describe the creation of a genetic construct suitable to be transformed by particle bombardment. However, there are other means of transforming plants, and creating transgenic plants, which require many different vector systems, such as transformation using *Agrobacterium tumefaciens* and electroporation. The ability to construct and adopt such vectors is well known in the art.

EXAMPLES

Isolation of D5 cDNA

Total RNAs from young spikes, measuring 5 cms, and flag leaves of barley (cv. Morex, Small Grains Germplasm Research Facility, Aberdeen, Id.) were isolated as described by Chirgwin et al., "Isolation of Biologically Active Ribonucleic Acid From Sources Enriched In Ribonuclease," *Biochemistry,* 18:5294–99 (1979). Using an oligo-dT cellulose column (Type III, Collaborative Biomedical Products, Bradford, Mass.), mRNA was isolated from the total RNA. Synthesis of first strand spike and leaf cDNAs was carried out according to Krug and Berger, "First-Strand cDNA Synthesis Primed with Oligo(dT)," *Methods in Enzymology,* 152:316–325 (1987).

Differential display of cDNAs was performed as described by Miele et. al., "Elimination of False Positives Generated Through PCR Re-Amplification of Differential Display cDNA," *BioTechniques*, 25:138–144 (1998), with modifications. The volumes of first strand cDNAs were each brought up to 332.5 μl using sterile water, and 1 μl of this was used as a template for differential display analysis. A non-radiolabeled primary polymerase chain reaction (PCR) was performed in a 25 μl final volume using 40 μM each of dNTPs; 10 mM Tris-Cl, pH 8.3, 1.5 mM $MgCl_2$, 50 mM KCl; 400 pM ETVN primer (21 mer); 1.29 μM RAPD primer (10 mer); and 1.5 units of Taq DNA Polymerase. The thermal cycling parameters were: 94° C., 1 min 45 sec, 1 cycle; 94° C., 30 sec, 42° C., 30 sec, 72° C., 1 min, 25 cycles; 72° C., 7 min, 1 cycle; and soak cycle at 4° C.

A 35 cycle, radiolabeled secondary PCR was performed essentially as above, and included 6 μl of the primary PCR product, 0.5 μl of 10 mCi/ml $\alpha$-[35]S dATP. The differential display products were separated electrophoretically in a 6% denaturing polyacrylamide gel, and autoradiographed using Kodak X-OMAR AR film (Eastman Kodak Company, New Haven, Conn.).

Cloning of D5 cDNA

Several cDNAs from genes expressed in spike tissues, but not leaves, were observed and sliced out of the gel and placed in 1 ml of sterile water for 15 minutes to leach out urea. Pieces of this cDNA-containing gel were then used as templates for PCR amplifications. Reactions were performed as described above in 5 replicates of 40 μl volume each. Amplified cDNAs were precipitated with ethanol and each PCR product was resuspended in 11 μl $dH_2O$ where they were digested with Hpa II and Taq I. The digested cDNAs were electrophoretically separated in a 3% NuSieve GTG Agarose gel (FMC BioProducts, Rockland, Me.) in 1×TBE (0.09 M Tris-Borate; 0.002 M NaEDTA).

A unique cDNA band was observed in several spike lanes but not in the leaf lanes. This cDNA band was extracted from the agarose gel with AgarACE and designated as D5. This D5 cDNA was then precipitated using ethanol, resuspended in water and made blunt-ended using T4 DNA Polymerase. The D5 cDNA fragment was then further purified electrophoretically in a 1% SeaPlaque Agarose (FMC BioProducts) gel in 1×TAE (0.04 M Tris-acetate, 0.001 M NaEDTA), and extracted using AgarACE. The Blunt-ended D5 cDNA was then ligated into the Sma I site of pBluescript SK (Stratagene, La Jolla, Calif.), and used to transform *E. coli* DH5α cells. Colonies containing the recombinant plasmid were selected on LB plates containing Ticillin and X-gal. Plasmid DNA was isolated from liquid cultures according to Bimboin and Doly, "A Rapid Alkaline Extraction Procedure For Screening Recombinant Plasmid DNA," *Nucleic Acids Research*, 15:1513–1523 (1979).

Characterization of the D5 cDNA

Using about 100 ng of blunt-ended D5 cDNA as a template, an $\alpha$[32]PdCTP radiolabeled probe was prepared using the random hexamers method (Feinberg and Vogelstein, "A Technique For Radiolabeling DNA Restriction Endonuclease Fragments to High Specific Activity," *Analytical Biochemistry*, 132:6–13 (1983); Feinberg and Vogelstein, "Addendum: A Technique For Radiolabeling DNA Restriction Endonuclease Fragments to High Specific Activity," *Analytical Biochemistry*, 137:266 (1984)). RNA gel blots and DNA (Southern) gel blots were prepared using the protocols described by Sambrook, et al., *Molecular Cloning: A Laboratory Manual: Second Edition* (Cold Spring Harbor, N.Y., Cold Spring Harbor Laboratory, 1989). Blots were pre-hybridized overnight at 42° C., and were hybridized with radiolabeled probe (1 million cpm/ml) for 24 hours at 42° C. Blots were washed three times at low stringency (2×SSC, 0.1% SDS, room temperature, 15 min), two more times at high stringency (0.2×SSC, 0.1% SDS, 65° C., 15 min), and finally were washed briefly with 2×SSC at room temperature. The blots were autoradiographed for 72 hours using Kodak X-Omar AR film.

The D5 clone was selected based on its high expression levels in spike tissue as determined by the RNA gel blot analysis, and the clone was sequenced. The cDNA sequence revealed little homology to other reported genes.

Cloning of the D5 Promoter from a Barley Genomic BAC Library

The D5, spike-specific cDNA clone isolated from the above efforts, was used as a probe to search a Barley genomic BAC Library for corresponding BAC clones. (Provided by Dr. A. Kleinhofs, (Washington State U.) as part of the North American Barley Genome Mapping Project.) This screening yielded one clone.

The single D5 BAC clone was trimmed down into smaller fragments using DNA restriction enzymes. The D5 BAC clone was first digested with Eco RI, and a DNA fragment corresponding to the D5 clone was subcloned into the Eco RI site of pBluescript SK (pBACD5 EcoRI-EcoRI, FIG. 1). A Pst I fragment was then removed from this clone, resulting in a smaller clone (pBACD5 EcoRI-PstI, FIG. 1) which was subsequently digested with Sma I to release a DNA fragment corresponding to the D5 genomic clone. This fragment was subcloned into the Sma I site of pBluescript SK (pBACD5 SmaI-SmaI:L1, FIG. 1) to yield a 2.8 kb SmaI-SmaI fragment, which was sequenced and analyzed.

To predict all possible open reading frames the sequence was analyzed using a bioinformatic program available on the Internet (www.ncbi.nlm.nih.gov/gorf/gorf.html; http://dot.imgen.bcm.tmc.edu:9331/seq-search/gene-search.html), resulting in the observation that the D5 genomic clone was located in one of the predicted open reading frames. A BLAST analysis as described by Altschul, et. al., "Gapped BLAST and PSI-BLAST: A New Generation of Protein Database Search Programs," *Nucleic Acids Res.*, 25:3389–3402 (1997) was performed using a 107 residue sequence from this D5 open reading frame. This analysis revealed that the D5 genomic clone shared a limited sequence homology with a rice anther-specific gene (RTS2) product (GenBank gi:607895). Specifically, the analysis established 33 identical residues and 37 positive residues out of a stretch of 74 residues containing 6 gaps (44% identical, 49% positive, and 8% gap, respectively). Further analysis of the sequence upstream of this open reading frame also exposed a promoter sequence with a score of 0.91 (data not shown). Similarly, a BLAST analysis based on the 1434 bp sequence from the D5 promoter sequence divulged 84% identical and positive bases, after opening a 2% gap in a stretch of 76 bases with the rice anther specific (RTS2) gene (U12171). Thus, it was deduced that the D5 genomic clone represented a unique plant promoter which had not yet been identified.

Construction of the D5 Promoter Expression Vector

The 1435 bp Hind III-Apa I fragment from pBACD5 SmaI-SmaI:L1 (FIG. 1) containing the D5 promoter and partial N-terminal coding region was subcloned, and inserted into a psGFP14 vector (Kaeppler et al., "Cereal Monocot Transformation Via Visual Selection of Cells Expressing Green Fluorescent Protein," *Plant Cell Reports*, In Press (2000)) containing a protein coding region for green flourescent protein (GFP), replacing the Ubi1 promoter contained in the vector's Hind III-B am HI fragment. The open reading frame between the D5 N-terminal and sGFP was restored by removing four bases at the D5/sGFP junction. This vector, pUCD5SGFP (FIG. 1), was used for transient expression study in plant tissues by the particle bombardment method. The vector psGFP14 (FIG. 1) was used as a positive control in testing the particle bombardment method.

Transient sGFP Expression Analysis in Barley

The tissue-specific expression of sGFP under the control of the D5 promoter was studied using a transient expression assay on immature barley spikes and flag leaf samples harvested prior to pollination. The spikes and leaves were transformed separately using the biolistic method with pUCD5SGFP or psGFP14 plasmids.

The transformation of barley tissue was carried out with a modification of the particle bombardment conditions described by Wan and Lemaux, "Generation of Large Numbers of Independently Transformed Fertile Barley Plants," *Plant Physiology*, 104:37–48 (1994).

Prior to transformation, the spikes and leaves were sterilized with 20% bleach for 20 min., followed by 95% ethanol for 30 seconds, and rinsed with sterile water. Osmotic shock treatment of the tissues (Vain et al. 1993) was performed by placing the tissues in osmotic solution (1.5% maltose, 6.4% mannitol, 6.4% sorbitol) for 3 hours before bombardment. The tissues were bombarded using a Biolistic PDS-1000 He gun (Bio-Rad, Hercules, Calif.) with 0.40 mg gold particles measuring 1 µm in diameter.

Macrocarriers were prepared as follows: 1.5 mg of gold particles, suspended in 220 µl of sterile water, were mixed with 25 µl of plasmid DNA (1 µg/µl concentration), followed by addition of 250 µl of 2.5 M $CaCl_2$ and 50 µl of 0.1 M spermidine. The mixture was gently vortexed for 10 minutes at 4° C. and then centrifuged briefly. The gold particles were washed with 100% ethanol and resuspended in 36µl of 100% ethanol. For each bombardment, 10 µl of the DNA coated gold particles was used. The spike tissues were bombarded twice at 1350 psi, and the leaves were bombarded once at 1100 psi.

The transformed tissues were incubated at 24°±1° C. for up to 72 hours. The tissues were observed for the expression of GFP during the subsequent 1 to 5 days. Expression of GFP in bombarded tissues was monitored using Zeiss Stemi-2000-C (Carl Zeiss, Inc., Thornwood, N.Y.) binocular microscope with short-wave blue light. Transformation events were recorded with Kodak Elitechrome film using Zeiss MC80 camera attachments.

The spikes and leaves expressed GFP within 12 hours of transformation with the constitutive promoter-containing control vector, psGFP14. The expression of GFP peaked after 48 hours in the spike tissues transformed with pUCD5SGFP. The leaves transformed with pUCD5SGFP did not express GFP even after 5 days, indicating that the D5 promoter is a good spike-specific promoter capable of providing expression of heterologous genes specifically in spike tissues.

What is claimed is:

1. A genetic construct comprising a spike tissue-specific promoter from SEQ ID NO:1 and a protein-coding sequence not natively associated with the spike tissue-specific promoter.

2. The genetic construct of claim 1 wherein the protein-coding sequence encodes an anti-fungal gene.

3. The genetic construct of claim 2, wherein the protein-coding sequence encodes a gene which confers resistance to *Fusarium graminearum.*

4. The genetic construct of claim 3 wherein the protein-coding sequence encodes thionin.

5. A plant cell comprising the genetic construct of claim 1.

6. A plant seed comprising the genetic construct of claim 1.

7. A genetic construct comprising a fragment of SEQ ID NO:1 and a protein-coding sequence not natively associated with SEQ ID NO:1 wherein said fragment promotes the expression of said protein-coding sequence in spike tissue.

8. The genetic construct of claim 7, wherein the protein-coding sequence encodes an anti-fungal gene.

9. The genetic construct of claim 8, wherein the protein-coding sequence encodes a gene which confers resistance to *Fusarium graminearum.*

10. The genetic construct of claim 9, wherein the protein-coding sequence encodes thionin.

11. A plant cell comprising the genetic construct of claim 7.

12. A plant seed comprising the genetic construct of claim 7.

* * * * *